United States Patent [19]

Hertenstein et al.

[11] Patent Number: 5,481,024
[45] Date of Patent: Jan. 2, 1996

[54] PROCESS FOR THE PREPARATION OF MONOMERIC TEREPHTHALIC DIESTERS AND DIOLS FROM POLYESTERS

[75] Inventors: Ulrich Hertenstein, Gablingen; Rudolf Neugebauer, Meitingen, both of Germany

[73] Assignee: Hoechst Aktiengesellschaft, Frankfurt, Germany

[21] Appl. No.: 107,236

[22] Filed: Aug. 16, 1993

[30] Foreign Application Priority Data

Aug. 18, 1992 [DE] Germany .................. 42 27 299.8

[51] Int. Cl.⁶ .................................................. C07C 67/48
[52] U.S. Cl. .................................................. 560/78; 560/98
[58] Field of Search ............................. 560/78, 98

[56] References Cited

U.S. PATENT DOCUMENTS 2,884,443  4/1959  Siggel et al. .
3,037,050  5/1962  Heisenberg et al. .
3,257,335  6/1966  Whitfield et al. ................. 260/2.3
3,321,510  5/1967  Lotz et al. .
3,776,945  12/1973  Ligorati et al. .
5,051,528  9/1991  Naujokas et al. ................. 560/78

FOREIGN PATENT DOCUMENTS 1003714  3/1957  Germany .

*Primary Examiner*—José G. Dees
*Assistant Examiner*—Samuel Barts
*Attorney, Agent, or Firm*—Connolly and Hutz

[57] ABSTRACT

The invention relates to a novel process for the preparation of terephthalic diesters and diols from polyesters. The process comprises depolymerization of the polyester in the presence of transesterification catalysts for said polyester and in the presence of an ester and subsequent transesterification of the reaction mixture to give the terephthalic diester by reaction with a monohydric alcohol. The novel process allows the starting components of polyesters to be recovered rapidly and under mild reaction conditions.

20 Claims, No Drawings

PROCESS FOR THE PREPARATION OF MONOMERIC TEREPHTHALIC DIESTERS AND DIOLS FROM POLYESTERS

DESCRIPTION

Process for the preparation of monomeric terephthalic diesters and diols from polyesters.

The present invention relates to a novel process for the preparation of terephthalic diesters and diols from polyester waste.

In addition to polyethylene terephthalate (referred to as PET below), other polyesters are also commercially available. The term "polyester" hereinafter is taken to mean a polyester whose acid component contains at least some terephthalic acid units.

Of the approximately 16 million tonnes of PET now produced worldwide per annum, only an insignificant proportion is subjected to chemical recycling. On the other hand, polyester takes up a large proportion of waste disposal capacity. The re-use of polyesters as polymers after use is only possible to a limited extent, i.e. only relatively small amounts can be used for low-quality applications ("downcycling").

There is thus a demand for suitable processes for chemically degrading polyesters in such a way that the monomers isolated therefrom can be employed, after purification, in the same way as conventional raw materials ("up-cycling").

In principle, polyester can be converted into terephthalic acid or into a diester of terephthalic acid, such as, for example, into dimethyl terephthalate (referred to as DMT below). Terephthalic acid can only be purified by recrystallization and/or adsorption, filtration of the entire solution being extremely technically complex for large throughputs. Low-solubility impurities can therefore not be removed from terephthalic acid to the necessary extent, which restricts the utility of the terephthalic acid produced. DMT can be both recrystallized and distilled, and can therefore, even if produced from PET, be adjusted to the purity necessary in the polycondensation process of high-quality grades.

Since the recycling of polyesters via DMT is superior to recycling via terephthalic acid due to the fact that purification can be carried out more favorably, an economical process has been sought which operates continuously and can convert large amounts of polyesters under the mildest possible conditions.

It is known that polyesters can be degraded to DMT by means of methanol at temperatures between 100° and 300° C. and at pressures of up to 150 atm (U.S. Pat. No. 3,776,945). This process has the disadvantage that very long reaction times and high pressures must be used. This problem can be alleviated both by using steam (U.S. Pat. No. 3,321,510) and by using transesterification catalysts (U.S. Pat. No. 3,037,050).

DE-A-1,003,714 describes that the degradation of polyesters to DMT by means of methanol and transesterification catalysts can be greatly accelerated by the presence of DMT. Analogously, U.S. Pat. No. 5,051,528 describes that the conversion of PET to DMT by means of methanol in the presence of transesterification catalysts is accelerated by adding the PET to oligomers and simultaneously treating the mixture with supercritical methanol vapor. The reaction is carried out in such a way that DMT, glycol and excess methanol are removed by distillation. Non-volatile constituents in the PET therefore accumulate in the reactor. If the reaction is carried out continuously, a large purging stream is therefore unavoidable.

The previously known processes for recovery of the acid and alcohol components from polyesters thus involve the use of complex process measures. Thus, U.S. Pat. No. 5,051,528 states that solid PET must be introduced into a pressurized reactor containing supercritical methanol if the reaction is to be carried out continuously. According to DE-A-1,003,714, a continuous procedure is not possible.

It is common to both processes that the degradation of PET is carried out by means of methanol in the presence of DMT or oligomers.

On the basis of these previously known processes, the present invention had the object of developing a process which is capable of converting large amounts of polyesters into terephthalic diesters and diols, in particular into DMT and ethylene glycol, rapidly and under the mildest possible conditions while avoiding the above-described process difficulties and which can particularly advantageously be operated continuously.

Surprisingly, it has now been found that polyesters can be depolymerized by means of esters of monohydric alcohols in the presence of transesterification catalysts, the depolymerization preferably being carried out at atmospheric pressure. From, for example, DMT and PET in a stoichiometry of 1:1, based on the aromatic compound, this process gives dimethylethylene diterephthalate (referred to as DMEDT below). If DMT is employed in a substoichiometric amount relative to PET, oligomers containing terminal methoxycarbonyl groups are obtained. Oligomers and DMEDT can be transesterified in a transesterification equilibrium with methanol to give DMT. It has been found that the depolymerization step is greatly accelerated by the presence of a transesterification catalyst. If the reaction between the polymer and the ester is carried out in the presence of transesterification catalysts, the reaction can even take place at atmospheric pressure and, depending on the predetermined reaction temperature, can be complete within minutes. By separating the two reactions, polymer degradation and transesterification, a continuous process using simple technology can be developed.

The invention therefore relates to a two-step process for the preparation of monomeric terephthalic diesters and diols by depolymerization of a polyester by means of esters of monohydric alcohols in the presence of transesterification catalysts, and subsequent transesterification of the depolymer by means of a monohydric alcohol.

In order to carry out the process according to the invention, PET granules are introduced, for example into a DMT melt in the presence of transesterification catalysts, preferably at atmospheric pressure; the majority of the adhering water is evaporated. The transesterification catalysts may originate from the PET granules and/or be added thereto. The granules dissolve with degradation, giving a pumpable melt. The latter is fed to a transesterification reactor, into the bottom of which methanol gas is introduced. The excess methanol and the ethylene glycol formed are removed at the top of the reactor, while DMT and impurities from the PET are withdrawn at the bottom. The bottom product is further purified by distillation. The top product is separated into its components by distillation.

An essential advantage of this process is the fact that the majority of the water introduced during the depolymerization is evaporated. Partial hydrolysis occurs, with liberation of methanol. The acids formed are re-esterified in the transesterification step with formation of water. In the one-step process of U.S. Pat. No. 5,051,528, by contrast, all the water introduced with the PET granules forms with the methanol/glycol mixture and must be removed by distillation.

As the starting material, any terephthalic acidcontaining polyesters can be employed, i.e. homo- or copolyesters which contain terephthalic acid as the acid component. Preferred examples are polybutylene terephthalate and in particular polyethylene terephthalate. Examples of copolyesters are copolyethylene terephthalates which contain aliphatic dicarboxylic acids, such as adipic acid or sebacic acid, as the acid component in addition to terephthalic acid and ethylene glycol, and/or which contain aliphatic diols, such as diethylene glycol or butylene glycol, as the alcohol components.

The ester employed in the depolymerization step is preferably an alkyl ester, in particular a dialkyl ester, of an aromatic dicarboxylic acid.

Examples of alkyl esters are alkyl esters of aliphatic, cycloaliphatic, araliphatic or in particular aromatic mono- or dicarboxylic acids. Preference is given to esters containing alkyl groups having one to six carbon atoms, in particular ethyl esters and very particularly methyl esters.

Examples of suitable acid components for the alkyl esters are formic acid, acetic acid, propionic acid, burytic acid, adipic acid, sebacic acid and cyclohexanecarboxylic acid. Particularly suitable acid components for the alkyl esters are aromatic dicarboxylic acids, such as isophthalic acid, phthalic acid and in particular terephthalic acid.

Examples of particularly preferred esters are dimethyl isophthalate and very particularly dimethyl terephthalate.

The ester is preferably employed in an amount of from 0.5 to 10 mol, preferably from 1 to 5 mol, based on one mole of polyester.

It is also possible to employ mixtures of esters.

Transesterification catalysts which can be employed for the depolymerization are any compounds which are suitable for this purpose, or mixtures of such compounds.

Examples of preferred transesterification catalysts are manganese acetate, zinc oxide, zinc acetate, zinc chloride and magnesium oxide, or mixtures of these compounds, and other acidic transesterification catalysts.

The catalysts are expediently employed in amounts of from 10 to 500 ppm, based on the polyester.

It has been found that the depolymerization proceeds at a significant rate from the melting point of the ester employed. In the case of DMT, a depolymerization temperature of at least 140° C. is therefore selected. The reaction rate increases with temperature. The solubility of water in DMT decreases with temperature.

In the case of DMT, the temperature range chosen for the depolymerization is preferably from 140° to 300° C., in particular from 140° to 250° C. The reaction is complete within a few minutes, even when carried out at atmospheric pressure. The majority of the water introduced with the other reactants is removed by distillation.

The depolymerization can be carried out in solution or preferably in the melt; it can preferably be carried out at atmospheric pressure or under pressure, for example at a pressure of from 1 to 30 bar, preferably from 1 to 5 bar.

Examples of the solvents used are DMSO, DMF, N-methylpyrrolidone, hexamethylenephosphoric triamide or other solvents in which the polyester is at least partially soluble.

The progress of the reaction can expediently be followed by monitoring the melt viscosity or solution viscosity in the reaction mixture. The equilibrium in the melt is usually achieved as soon as the viscosity is in the region of the value for the ester employed, if such a stoichiometry is chosen so the PET can be fully degraded, i.e. at a DMT:PET stoichiometry of >1:1. The degradation in the first step, in particular in the case of continuous operation, can of course also be maintained at higher viscosity values.

To carry out the transesterification, virtually any monohydric alcohols or mixtures of monohydric alcohols, i.e. monohydric cycloaliphatic, araliphatic, aromatic or in particular aliphatic alcohols, can in principle be employed in the process according to the invention.

Examples of such alcohols are cyclohexanol, methylolcyclohexane, phenol, methanol, ethanol, propanol, butanol, pentanol and hexanol.

The transesterification step is preferably carried out using an alkyl alcohol having one to six carbon atoms, in particular methanol.

The monohydric alcohol is generally employed in an amount of from 2 to 20 mol, preferably from 5 to 10 mol, based on one mole of polyester. After separation from the diol formed, the monohydric alcohol is preferably circulated in the esterification step.

The transesterification step can be carried out at temperatures between 140° and 300° C. and at atmospheric pressure or under superatmospheric pressure, for example at between 1 and 20 bar.

The two process steps are very particularly preferably carried out continuously.

In a particularly preferred variant of the process according to the invention, some of the terephthalic diester obtained is fed back into the depolymerization step.

The examples below describe the process.

EXAMPLE 1

The following streams are metered simultaneously into a through-flow reactor: 3 mol of liquid DMT, one mole of PET granules and 300 ppm of manganese acetate. The reaction temperature is 200° C. and the mean residence time is 40 minutes.

The resultant product mixture of DMEDT in DMT is fed continuously to a transesterification column into the bottom of which methanol vapor is fed. A methanol/glycol mixture is taken off continuously at the top and partly serves as reflux and partly is separated into its components on a second column. Glycol is separated off; methanol is fed back into the transesterification column. DMT is withdrawn continuously from the bottom of the transesterification column; some of this DMT is fed back into the through-flow reactor and another part is fed to a rectification column.

EXAMPLE 2

The following streams are metered continuously into a through-flow reactor: 1.5 mol of DMT, one mole of PET granules and 400 ppm of solid manganese acetate. The reaction temperature is 180° C., and the reaction pressure is 5 bar. The mean residence time is 30 minutes. The resultant product mixture is further processed continuously as described in Example 1.

We claim:

1. A two-step process for the preparation of terephthalic diesters and diols by depolymerization of a polyester in the presence of transesterification catalysts for said polyester, which comprises carrying out the depolymerization in the presence of an ester in a first reactor and subsequently converting the mixture obtained in the first reactor in another reactor into terephthalic diester and diol by transesterification by means of a monohydric alcohol.

2. The process as claimed in claim 1, wherein the polyester employed is polyethylene terephthalate.

3. The process as claimed in claim 2, wherein the depolymerization is carried out at temperatures between 140° and 250° C. at atmospheric pressure in the presence of the following transesterification catalyst or catalysts: manganese acetate, zinc oxide, zinc acetate, zinc chloride or magnesium oxide, or a mixture of these compounds.

4. Process as claimed in claim 3, wherein the depolymerization step and the transesterification step are carried out continuously.

5. The process as claimed in claim 4, wherein the ester is dimethyl terephthalate.

6. The process as claimed in claim 3, wherein the depolymerization is carried out at temperatures between 140° and 200° C.

7. The process as claimed in claim 1, wherein the ester employed in the depolymerization step is an alkyl ester.

8. The process as claimed in claim 7, wherein the ester employed in the depolymerization step is a dialkyl ester of an aromatic dicarboxylic acid.

9. The process as claimed in claim 4, wherein the ester is dimethyl terephthalate.

10. The process as claimed in claim 1, wherein the transesterification step is carried out in the presence of a transesterification catalyst, said transesterification catalyst being manganese acetate, zinc oxide, zinc acetate, zinc chloride or magnesium oxide, or a mixture of these compounds.

11. The process as claimed in claim 1, wherein the depolymerization is carried out in the melt, and reaction monitoring is carried out by measuring the melt viscosity of the depolymerization reaction mixture.

12. The process as claimed in claim 1, wherein the monohydric alcohol in the transesterification step is an alkyl alcohol having one to six carbon atoms.

13. The process as claimed in claim 12, wherein the alkyl alcohol is methanol.

14. The process as claimed in claim 1, wherein the transesterification is carried out at temperatures between 140° and 300° C. and at pressures between 1 and 20 bar.

15. The process as claimed in claim 1, wherein excess monohydric alcohol is removed from the transesterification step by distillation together with the diol originating from the polyester, and the terephthalic diester remaining in the residue is subsequently purified by distillation.

16. The process as claimed in claim 1, wherein the depolymerization step and the transesterification step are carried out continuously.

17. The process as claimed in claim 1, wherein some of the terephthalic diester obtained is fed back into the depolymerization step.

18. A two-step continuous process for the preparation of terephthalic diesters and diols by depolymerization of a polyester in the presence of transesterification catalysts for said polyester, which comprises carrying out the depolymerization in the presence of an ester in a first reactor at atmospheric pressure or under a low pressure of up to 30 bar and at temperatures between 140° and 300° C., and subsequently converting the mixture obtained in the first reactor in another reactor into terephthalic diester and diol by transesterification by means of a monohydric alcohol and optionally removing excess monohydric alcohol from the transesterification step by distillation together with the diol originating from the polyester.

19. The process as claimed in claim 18, wherein methanol is added in the second step.

20. The process as claimed in claim 19, wherein the depolymerization step and the transesterfication step are carried out continuously.

* * * * *